(12) United States Patent
Yamada

(10) Patent No.: US 7,901,556 B2
(45) Date of Patent: Mar. 8, 2011

(54) GAS SENSOR EQUIPPED WITH COVER ASSEMBLY DESIGNED TO MINIMIZE SPLASHING OF SENSOR ELEMENT WITH WATER

(75) Inventor: Kouhei Yamada, Oobu (JP)

(73) Assignee: Denso Corporation, Kariya (JP)

( * ) Notice: Subject to any disclaimer, the term of this patent is extended or adjusted under 35 U.S.C. 154(b) by 975 days.

(21) Appl. No.: 11/790,581

(22) Filed: Apr. 26, 2007

(65) Prior Publication Data
US 2007/0251823 A1 Nov. 1, 2007

(30) Foreign Application Priority Data

Apr. 27, 2006 (JP) .................. 2006-124074
Nov. 15, 2006 (JP) .................. 2006-309297

(51) Int. Cl.
*G01N 27/407* (2006.01)
(52) U.S. Cl. ........ 204/428; 204/424; 204/429; 73/23.31; 73/23.32
(58) Field of Classification Search .......... 204/424–429; 73/23.31, 23.32, 31.05
See application file for complete search history.

(56) References Cited

U.S. PATENT DOCUMENTS

| 5,800,689 | A | 9/1998 | Hori et al. | |
|---|---|---|---|---|
| 6,279,376 | B1 | 8/2001 | Yamada et al. | |
| 6,749,732 | B2 | 6/2004 | Nakagawa et al. | |
| 7,159,447 | B2 | 1/2007 | Nakagawa | |
| 7,708,869 | B2 * | 5/2010 | Yamada | 204/428 |
| 2004/0144645 | A1 * | 7/2004 | Yamada et al. | 204/424 |
| 2005/0178187 | A1 * | 8/2005 | Nakagawa | 73/31.05 |
| 2005/0241937 | A1 * | 11/2005 | Shichida et al. | 204/424 |
| 2009/0020425 | A1 * | 1/2009 | Yamada | 204/426 |

FOREIGN PATENT DOCUMENTS

| JP | 4-11461 | 1/1992 |
|---|---|---|
| JP | 9-196888 | 7/1997 |
| JP | 11-183425 | 7/1999 |
| JP | 2000-171429 | 6/2000 |
| JP | 2003-207479 | 7/2003 |
| JP | 2005-227179 | 8/2005 |

* cited by examiner

*Primary Examiner* — Nam X Nguyen
*Assistant Examiner* — Susan Thai
(74) *Attorney, Agent, or Firm* — Nixon & Vanderhye PC

(57) ABSTRACT

A gas sensor is equipped with a cover assembly made up of an outer cover and an inner cover in which a gas sensor element is disposed. The outer cover has an outer gas inlet and an outer gas outlet formed closer to a top end of the cover assembly than the outer gas inlet. The inner cover has an inner gas inlet formed closer to the top end of the cover assembly than the outer gas inlet. The inner gas inlet is oriented to minimize the entry of drops of water having entered along with a gas to be measured into the inner cover to avoid splashing of the gas sensor element with the water.

12 Claims, 17 Drawing Sheets

TOP END SIDE

GAS SENSOR EQUIPPED WITH COVER ASSEMBLY DESIGNED TO MINIMIZE SPLASHING OF SENSOR ELEMENT WITH WATER

CROSS REFERENCE TO RELATED DOCUMENT

The present application claims the benefit of Japanese Patent Application Nos. 2006-124074 filed on Apr. 27, 2006 and 2006-309297 filed on Nov. 15, 2006, disclosures of which are incorporated herein by reference.

BACKGROUND OF THE INVENTION

1. Technical Field of the Invention

The present invention relates generally to a gas sensor which may be installed in an exhaust system of an internal combustion engine to determine the concentration of $O_2$, an air-fuel ratio, or the concentration of NOx in exhaust emissions, and more particularly to an improved structure of such a type of gas sensor equipped with a cover assembly designed to avoid the breakage of a sensor element arising from splashing with water without sacrificing a response speed of the gas sensor.

2. Background Art

FIG. 19 illustrates a typical example of an oxygen sensor 9 (also called $O_2$ sensor) which is to be installed in an exhaust pipe of an automotive internal combustion engine (not shown) to measure the concentration of oxygen ($O_2$) contained in exhaust gas G as a function of the air-fuel ratio of a mixture charged into the engine for use in controlling the combustion in the engine.

The oxygen sensor 9 includes a gas sensor element 92 and a protective cover assembly 93. The gas sensor element 92 is equipped with a solid electrolyte body made of zirconia and disposed within the protective cover assembly 93. The protective cover assembly 93 is made of metal such as stainless steel and has formed therein gas inlets 933 through which the exhaust gas G is admitted inside the protective cover assembly 933.

The exhaust gas G enters the protective cover assembly 93 at the gas inlets 933 and reaches the gas sensor element 92. The gas sensor element 92 is sensitive to the exhaust gas G to produce a signal as a function of the concentration of oxygen.

During the rest of the engine, the moisture contained in the exhaust gas G may touch on a cooled inner wall of the exhaust pipe cooled so that it is condensed into drops of water. When the temperature of the exhaust gas G is low immediately after the start-up of the engine, the drops of water may be blown away by the exhaust gas G without being evaporated and enter the protective cover assembly 93 together with the exhaust gas G.

The correct measurement of the concentration of oxygen requires keeping the gas sensor element 92 at high temperatures of 400° C. or more, i.e., at an activated state. The adhesion of the drops of water to the surface of the gas sensor element 92 within the protective cover assembly 93 may, thus, cause the gas sensor element 92 to be subjected to thermal stress and broken.

In order to minimize the adhesion of water to the gas sensor element 92, the protective cover assembly 93 is, as clearly illustrated in FIG. 19, made to have a double-wall structure equipped with an inner cover 931 and an outer cover 932 and also have the gas inlets 933 of the inner cover 931 placed in misalignment with those of the outer cover 932 in a direction of flow of the exhaust gas G.

However, when the water drops W are, as illustrated in FIG. 19, adhered to the outer surface 934 of the outer cover 932, they may move on the outer surface 934 to the gas inlets 933 and enter inside the outer cover 931. The water drops W may further slide on the outer surface 936 of the inner cover 931 or the inner surface 935 of the outer cover 932 to the gas inlets 933 of the inner cover 931 and then enters inside the inner cover 931, so that they stick to the gas sensor element 92, thereby resulting in breakage of the gas sensor element 92.

In order to avoid the above problem, Japanese Patent First Publication No. 8-240559 teaches, as illustrated in FIG. 20, the gas sensor element 92 covered with a water-repellant protective film 94 to resist the adhesion of the water to the gas sensor element 92.

The installation of the protective film 94 on the surface of the gas sensor element 92, however, will result in an increased time required for the exhaust gas G to reach a sensing portion of the gas sensor element 92, which leads to a delay in response of the gas sensor element 9. It also results in an increase in thermal capacity of the gas sensor element 92, thus prolonging the time required to bring the gas sensor element 92 into the activate state.

Japanese Utility Model First Publication No. 4-11461 teaches, as illustrated in FIG. 21, a gas sensor 90 equipped with a protective layer 940 formed on a protective cover 93 to cover gas inlets 933. When the protective layer 940 covers the gas inlets 933 too broadly, it will, like the above publication, will result in an increased time required for the exhaust gas G to reach a gas sensor element 920, which leads to a delay in response of the gas sensor element 9.

SUMMARY OF THE INVENTION

It is therefore an object of the invention to provide an improved structure of a gas sensor designed to avoid the breakage of a sensor element arising from splashing with water without sacrificing a response rate of the gas sensor.

According to one aspect of the invention, there is provided a gas sensor which may be employed in measuring the concentration of a specified gas contained in exhaust emissions of an internal combustion engine of an automotive vehicle. The gas sensor has a length with a base end and a top end opposite the base end and comprises: (a) a gas sensor element having a sensing portion sensitive to a concentration of a gas to be measured to provide a signal indicative thereof; (b) a housing having a base end and a top end opposite the base end, the housing having the gas sensor element retained therein; (c) a cover assembly having a base end and a top end which is opposite the base end and close to the top end of the gas sensor, the cover assembly including an outer cover and an inner cover disposed inside the outer cover, the cover assembly being joined at the base end thereof to the top end of the housing to place the sensing portion of the gas sensor element within the inner cover; (d) an outer gas inlet formed in a peripheral wall of the outer cover of the cover assembly; (e) an outer gas outlet formed in a portion of the outer cover of the cover assembly which is located closer to the top end of the cover assembly than the outer gas inlet; and (f) an inner gas inlet formed in a portion of the inner cover of the cover assembly which is located closer to the top end of the cover assembly than the outer gas inlet. The inner gas inlet is formed by an opening which is so shaped as to have an axial center line that is oriented from outside to inside the inner cover and defined to have a vertical quadrature component oriented in a rectangular coordinate system toward the base end of the gas sensor in an axial direction of the gas sensor.

The cover assembly, as described above, has the outer gas inlet and the outer gas outlet formed in the outer cover and the inner gas inlet formed in the portion of the inner cover which is located closer to the top end of the cover assembly than the outer gas inlet, thus causing the gas to be measured (will also called a measurement gas below) coming from a lateral direction to be introduced from the outer gas inlet into a clearance between the outer cover and the inner cover. Most of the measurement gas travels toward the top end of the cover assembly and then goes out of the outer gas outlet, while the remaining portion thereof enters the inner cover at the inner gas inlet and then reaches the gas sensor element.

The inner gas inlet is located closer to the top end of the cover assembly than the outer gas inlet and shaped so as to have the axial center line which is oriented from outside to inside the inner cover and has the vertical quadrature component oriented toward the base end of the gas sensor. This causes the measurement gas having entered from the outer gas inlet to be split into an outer gas stream which goes relatively straight to the outer gas outlet and an inner gas stream which relatively curves or winds from the inner gas inlet to inside the inner cover, so that drops of water having entered between the outer cover and the inner cover along with the measurement are directed toward the outer gas outlet by inertia forces thereof and then drained from the outer gas outlet outside the cover assembly. This is because the drops of water are higher in specific gravity than the measurement gas and, therefore, carried by the outer gas stream going relatively straight to the outer gas outlet. The measurement gas which is lower in specific gravity than the drops of water partially enters the inner cover to produce the inner gas stream to which the gas sensor element is exposed. This avoids the entry of the drops of water into the inner cover without a delay in time required for the measurement gas to reach the gas sensor element, thus avoiding the breakage of the gas sensor element arising from splashing of water.

The outer gas stream, as referred to above, is a gas stream which is a portion of the flow of the measurement gas having entered at the outer gas inlet, goes to the outer gas outlet between the outer and inner covers, and is not necessarily oriented to flow straight.

The inner gas stream, as referred to above, is a gas stream which is split from the flow of the measurement gas having entered at the outer gas inlet, goes inside the inner cover independently from the outer gas stream, and is not necessarily oriented to flow in the curved form.

In the preferred mode of the invention, the outer gas outlet is formed in a top end of the outer cover. This avoids staying of water on an inner wall of the outer cover to ensure the durability of the gas sensor element.

The inner cover and the outer cover both have top ends which lie flush with each other to define the top end of the cover assembly. This minimizes the entry of water into the outer gas outlet along with the measurement gas.

The inner cover has a top end located far away from the base end of the cover assembly. The gas sensor further comprises an inner gas outlet form in the top end of the inner cover. The flow of the measurement gas passing outside and near the inner gas outlet hole produces the vacuum which facilitates the entry of the measurement gas having come inside the outer cover into the inner cover through the inner gas inlet with no drop of water.

The outer cover of the cover assembly has at least one wall having a diameter which decreases as approaching the top end of the cover assembly. For instance, the at least one wall may taper toward the top end of the cover assembly. This facilitates the production of a smooth stream of the measurement gas to the outer gas outlet between the outer and inner covers.

The inner cover of the cover assembly has at least one wall having a diameter which decreases as approaching the top end of the cover assembly. The at least one wall may taper toward the top end of the cover assembly. This also facilitates the production of a smooth stream of the measurement gas to the outer gas outlet between the outer and inner covers.

The at least one wall of the inner cover includes a portion of the inner cover which is the smallest in diameter and is located closer to the top end of the gas sensor than the top end of the gas sensor element facing the top end of the gas sensor. This minimizes the physical interference of the gas sensor element with an inner wall of the inner cover when the gas sensor element undergoes vibrations and swings.

The axial center line is defined to include the vertical quadrature component and a transverse quadrature component which is oriented perpendicular to the axial direction of the gas sensor. This serves to create a stream of the measurement gas which is introduced between the outer cover and the inner cover and enters inside the inner cover through the inner gas inlet and which is more complex, thus decreasing the possibility of entry of water to the inner cover through the inner gas inlet greatly.

The inner cover may have formed in a peripheral wall thereof a recess having a base end oriented toward the base end of the cover assembly. The inner gas inlet may be formed in the base end of the recess. This permits the inner gas inlet to be geometrically shaped to have the axial center line extending in parallel to the lengthwise direction of the cover assembly, thus decreasing the possibility of entry of water to the inner cover through the inner gas inlet.

The inner cover has a side surface which faces the outer gas inlet formed in the cover and extends in parallel to the lengthwise direction of the gas sensor. This facilitates the production of a smooth stream of the measurement gas in the axial direction of the gas sensor between the inner and outer covers, thus promoting the formation of a smooth flow of drops of water which are higher in specific gravity than the measurement gas in the lengthwise direction of the gas sensor and discharging it from the outer gas outlet.

The gas sensor element has affixed to a surface thereof a measurement gas electrode which is to be exposed to the gas to be measured. The measurement gas electrode having a length with a base end and a top end which is opposite the base end thereof and faces the top end of the cover assembly. The inner gas inlet is located within half the length of the measurement gas electrode from the base end of the measurement gas electrode. This ensures quick reach of the measurement gas having entered at the inner gas inlet to the measurement gas electrode and the exposure of the whole of the measurement gas electrode to the measurement gas, thereby enhancing the responsiveness of the gas sensor.

The axial center line also includes a transverse quadrature component which is oriented perpendicular to the axial direction of the gas sensor. The angle which the axial center line of the inner gas inlet makes with the transverse quadrature component is 5° or more, preferably 15° or more, and more preferably 30° or more.

According to the second aspect of the invention, there is provided a gas sensor having a length with a base end and a top end opposite the base end which comprises: (a) a gas sensor element having a sensing portion sensitive to a concentration of a gas to be measured to provide a signal indicative thereof; (b) a housing having a base end and a top end opposite the base end, said housing having said gas sensor element retained therein; (c) a cover assembly having a base end and a top end which is opposite the base end and close to the top end of the gas sensor, said cover assembly including an outer cover and an inner cover disposed inside the outer cover, said cover assembly being joined at the base end thereof to the top end of said housing to place the sensing portion of said gas sensor element within the inner cover; (d) an outer gas inlet formed in a peripheral wall of the outer cover of said cover assembly; (e) an outer gas outlet formed in a portion of the outer cover of said cover assembly which is located closer to the top end of said cover assembly than said outer gas inlet; and (f) an inner gas inlet formed in a portion of the inner cover of said cover assembly which is located closer to the top end of said cover assembly than said outer gas inlet. The outer and inner covers of said cover assembly are so shaped as to split a flow of the gas to be measured having entered from said outer gas inlet into an outer gas stream and an inner gas stream. The outer gas stream goes to said outer gas outlet between the outer and inner covers, while the inner gas stream goes inside the inner cover through the inner gas inlet.

In the preferred mode of the invention, the outer gas stream has a vector component which is oriented from the base end to the top end of said cover assembly, while the inner gas stream has a vector component which is oriented from the top end to the base end of said cover assembly.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
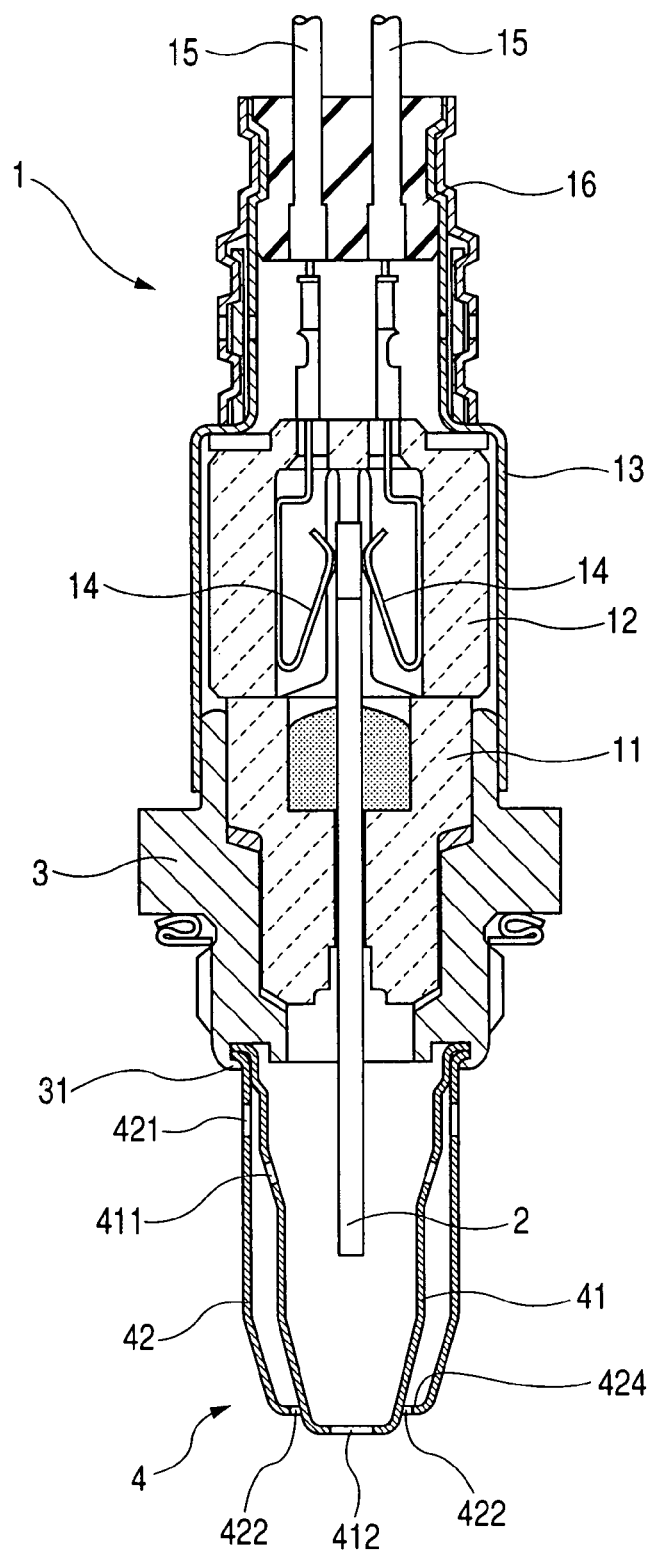
FIG. 1 is a longitudinal sectional view which shows a gas sensor equipped with a protective cover assembly according to the first embodiment of the invention.

Referring to the drawings, wherein like reference numbers refer to like parts in several views, particularly to FIG. 1, there is shown a gas sensor 1 according to the first embodiment of the invention which may be engineered as an A/F sensor to be installed in an exhaust pipe of an automotive internal combustion engine for use in an exhaust gas feedback system, an oxygen ($O_2$) sensor to measure the concentration of oxygen ($O_2$) contained in the exhaust gas, or a NOx sensor for use in monitoring the deterioration of a three-way catalyst installed in the exhaust pipe of the engine.

The gas sensor 1 generally includes a gas sensor element 2 sensitive to the concentration of a preselected component of gas (will also be referred to as a measurement gas below) to produce a signal indicative thereof, a hollow cylindrical housing 3 in which the gas sensor element 2 is retained, and a protective cover assembly 4 joined to a top end (i.e., a lower end, as viewed in FIG. 1) of the housing 3.

The protective cover assembly 4 has a length extending in alignment with the longitudinal center line of the gas sensor 1 (i.e., the gas sensor element 2). The protective cover assembly 4, as clearly illustrated in FIGS. 1 and 2, has a double-walled structure consisting of a cylindrical outer cover 42 and a cylindrical inner cover 41 disposed inside the outer cover 42. The outer cover 42 has a plurality of gas inlet holes 421 formed in a side wall thereof and a gas outlet hole 422 formed in the top end thereof. The inner cover 41 has formed in a side wall thereof gas inlet holes 411 which are located closer to the top end of the protective cover assembly 4 than the gas inlet holes 421 of the outer cover 42.

Figure 2:
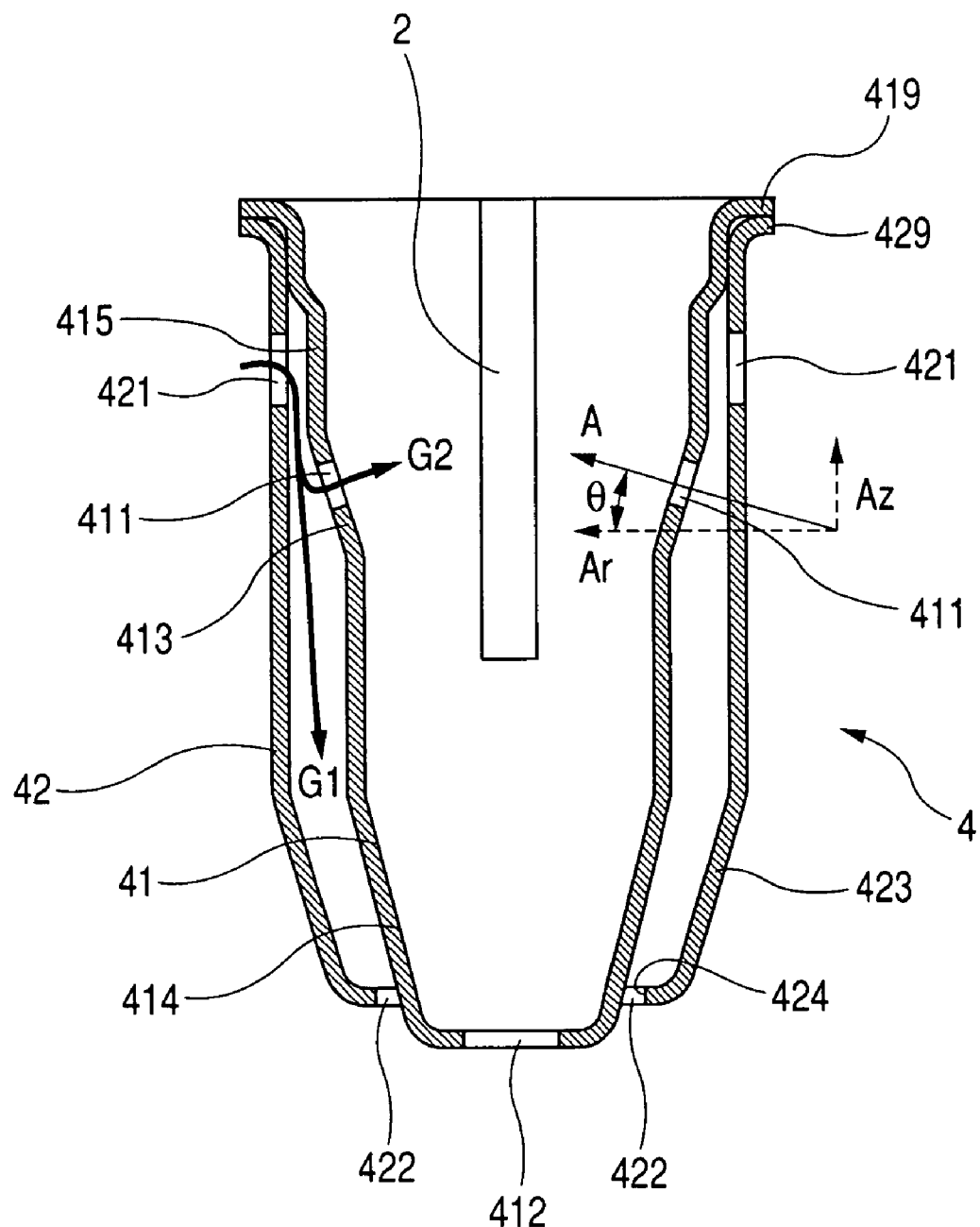
FIG. 2 is an enlarged view which shows the protective cover assembly in FIG. 1.

Each of the gas inlet holes 411 of the inner cover 41 is, as can be seen from FIG. 2, oriented to have an axial center line A that is a line extending perpendicular to a plane including an outline of the gas inlet hole 411 and defined by a vertical quadrature component Az and a transverse quadrature component Ar. The vertical quadrature component Az is oriented in a rectangular coordinate system toward the base end (i.e., an upper end, as viewed in FIG. 1) of the gas sensor 1 in parallel to a longitudinal center line (i.e., an axis) of the gas sensor 1 (or the gas sensor element 2). The transverse quadrature component Ar is oriented to the center of the gas sensor 1 perpendicular to the longitudinal center line of the gas sensor 1 (i.e., the gas sensor element 2). Specifically, the axial center line A represents the orientation of a flow of the measurement gas passing through each of the gas inlet holes 411.

The axial center line A of each of the gas inlet holes 411 is, as described above, defined to extend perpendicular to the plane including the outline of the gas inlet hole 411. If, however, each of the gas inlet holes 411 is shaped to have the outline partially protruding from the plane, the axial center line A is defined to extend perpendicular to an imaginary plane established to include a curved line which is the closest approximate to the outline of the gas inlet hole 411. The axial center line A will also be referred to as an opening orientation below.

The outer cover 42 has the gas outlet hole 422 formed in the top end thereof. Similarly, the inner cover 41 has a gas outlet hole 412 formed in the top end thereof.

The outer cover 42 has a frusto-conical wall 423 tapering toward the top end thereof. The inner cover 41 has two frusto-conical walls 413 and 414 tapering to the top end thereof. The tapered walls 413 and 414 are located away from each other in a lengthwise direction of the inner cover 41 and extend coaxially with each other. The tapered wall 413 has the gas inlet holes 411.

The inner cover 41 also has an annular upright wall 415 extending straight in parallel to the lengthwise direction of the gas sensor 1. The upright wall 415 faces the gas inlet holes 421 of the outer cover 42 so that a flow of the measurement gas entering at each of the gas inlet holes 421 may hit the upright wall 415.

The inner cover 41 is disposed in the outer cover 42 with the top end of the inner cover 41 protruding from the top end of the outer cover 42. Specifically, the outer cover 42 has formed in the top end thereof a large-diameter opening 424 which is greater in diameter than the top end of the inner cover 41. The top end of the inner cover 41 is inserted into the large-diameter opening 424 to define the gas outlet hole 422 between the outer periphery of the top end of the inner cover 41 and the inner periphery of the large-diameter hole 424 of the outer cover 42.

The end face of the inner cover 41 may alternatively lie in flush with or inside the end face of the outer cover 42.

The protective cover assembly 4 is, as clearly illustrated in FIG. 1, held by a nip formed by bending an annular extension 31 on the top end of the housing 3 inwardly. Specifically, the inner and outer covers 41 and 42 have, as clearly illustrated in FIG. 2, formed at base ends thereof flanges 419 and 429 which are placed within an annular groove formed in the top end of the housing 3 and retained tightly by crimping the annular extension 31 inwardly.

The housing 3, as illustrated in FIG. 1, has disposed therein a gas-side porcelain insulator 11 within which the gas sensor element 2 is retained. An atmosphere-side porcelain insulator 12 is placed on the base end of the gas-side porcelain insulator 11 in alignment with the length of the gas sensor 1. An air cover 13 is joined or welded to the base end of the housing 3 to surround the atmosphere-side porcelain insulator 12.

Metallic terminals 14 are retained inside the atmosphere-side porcelain insulator 12 to establish electrical connections with the gas sensor element 2. The terminals 14 connect with leads 15. The leads 15 extend outside the gas sensor 1 through a rubber bush 16 fitted hermetically in the base end of the air cover 13.

The gas sensor element 2 is of a typical structure including a solid electrolyte body made mainly of zirconia, a measurement gas electrode, a reference gas electrode, and a heater (all not shown). The measurement gas electrode and the reference gas electrode are affixed to opposed surfaces of the solid electrolyte body and connected to the leads 15. The measurement gas electrode is to be exposed to the measurement gas. The reference gas electrode is to be exposed to air used as a reference gas. In use of the gas sensor 1, the heater works to heat the solid electrolyte body (i.e., the gas sensor element 2) up to 400° C. to place the gas sensor element 2 in an activated state.

The features or advantages, as provided by the structure of the protective cover assembly 4, will be described below.

Figure 3:
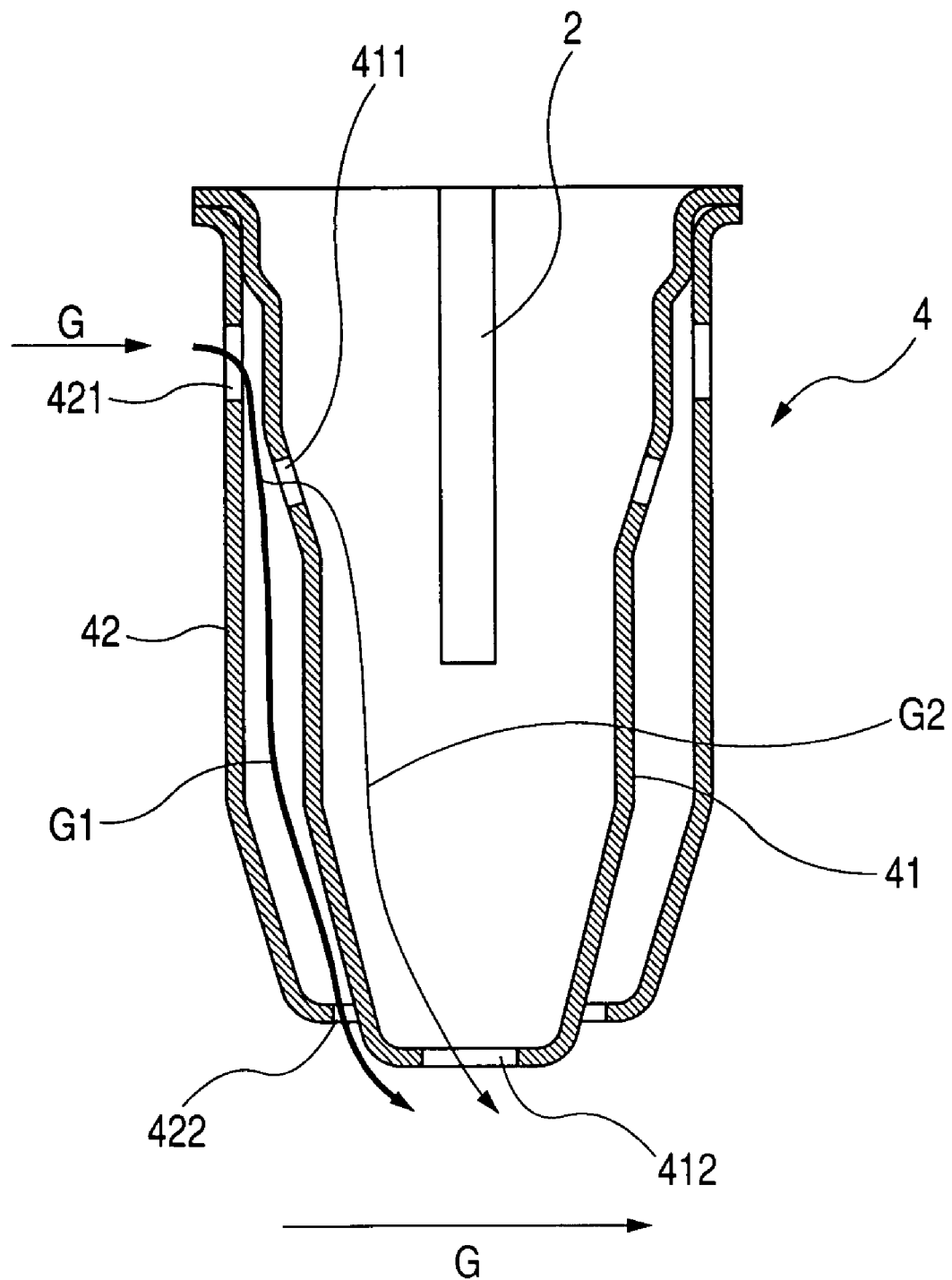
FIG. 3 is an enlarged view which shows flows of gas streams through the protective cover assembly of FIG. 1.

The protective cover assembly 4, as described above, has the outer gas inlet holes 421 and the gas outlet hole 422 formed in the outer cover 42 and the inner gas inlets 411 formed in a portion of the inner cover 41 which is located closer to the top end of the protective cover assembly 4 than the outer inlet holes 421, thus causing, as illustrated in FIG. 3, the measurement gas G coming from the lateral direction to be introduced from the outer gas inlet hole 421 into a clearance between the outer cover 42 and the inner cover 41. Most of the measurement gas G travels toward the top end of the protective cover assembly 4 as a relatively straight outer gas stream G1 and then goes out of the gas outlet hole 422, while the remaining portion thereof enters the inner cover 41 at the inner gas inlet hole 411 to create a relatively curving inner gas stream G2 to which the gas sensor element 2 is exposed. Each of the inner gas inlet holes 411 is, as described above, designed to have the axial center line A including the vertical quadrature component Az and the transverse quadrature component Ar, as defined in the rectangular coordinate system. The inner gas stream G2, thus, enters the inner cover 41 along the axial center line A. In other words, the flow of the inner gas stream G2 when passing through the inner gas inlet holes 411 has a vector component (i.e., the vertical quadrature component Az) which is oriented from the top end to the base end of the protective cover assembly 4 and opposite that of the outer gas stream G1.

The inner gas inlet holes 411 are, as described above, located closer to the top end of the protective cover assembly 4 than the outer gas inlet holes 421. Each of the inner gas inlets 411 is so geometrically shaped as to have the axial center line A which is oriented from outside to inside the inner cover 41 and has the vertical quadrature component Az oriented toward the base end of the gas sensor 1. This causes the measurement gas G having entered at one of the outer gas inlet holes 421 to be split into the outer gas stream G1 which goes almost straight to the gas outlet hole 422 and the inner gas stream G2 which relatively waves or winds from the inner gas inlet hole 411 to the gas outlet hole 412 of the inner cover 41.

Consequently, drops of water having entered between the outer cover 42 and the inner cover 41 along with the measurement gas G are directed toward the gas outlet hole 422 by inertia forces thereof and then drained from the gas outlet hole 422 outside the protective cover assembly 4. The measurement gas G which is lower in specific gravity than the drops of water partially enters the inner cover 41 as the inner gas stream G2 to which the gas sensor element 2 is exposed. This avoids the entry of the drops of water into the inner cover 41 without a delay in time required for the measurement gas G to reach the gas sensor element 2, thus avoiding the breakage of the gas sensor element 1 arising from splashing of water.

Specifically, the structure of the protective cover assembly 4 is geometrically designed to split the flow of the measurement gas G having entered at the outer gas inlet holes 421 into two discrete streams; one (i.e., the outer gas stream G1) oriented toward the gas outlet hole 422 outside the inner cover 41 and the other (i.e., the inner gas stream G2) entering inside the inner cover 41, thereby minimizing the entry of drops of water contained in the measurement gas into the inner cover 41 to avoid the breakage of the gas sensor element 1 arising from splashing of water.

In order to achieve the above effects, it is advisable that the angle θ, as illustrated in FIG. 2, which the axial center line A of each of the inner gas inlet holes 411 makes with the transverse quadrature component Ar be greater than or equal to 5°, preferably 15°, more preferably 30° in order to minimize the entry of the drops of water into the inner cover 41 to avoid the breakage of the gas sensor element 1 arising from splashing of water.

The protective cover assembly 4 has the outer gas inlet holes 421 and the inner gas inlet holes 411 oriented and located in a positional relation which minimizes the entry of drops of water into the inner cover 41, as described above, thus permitting a required amount of the measurement gas G to be introduced into the protective cover assembly 4 without sacrificing the response of the gas sensor 1.

Figure 20:
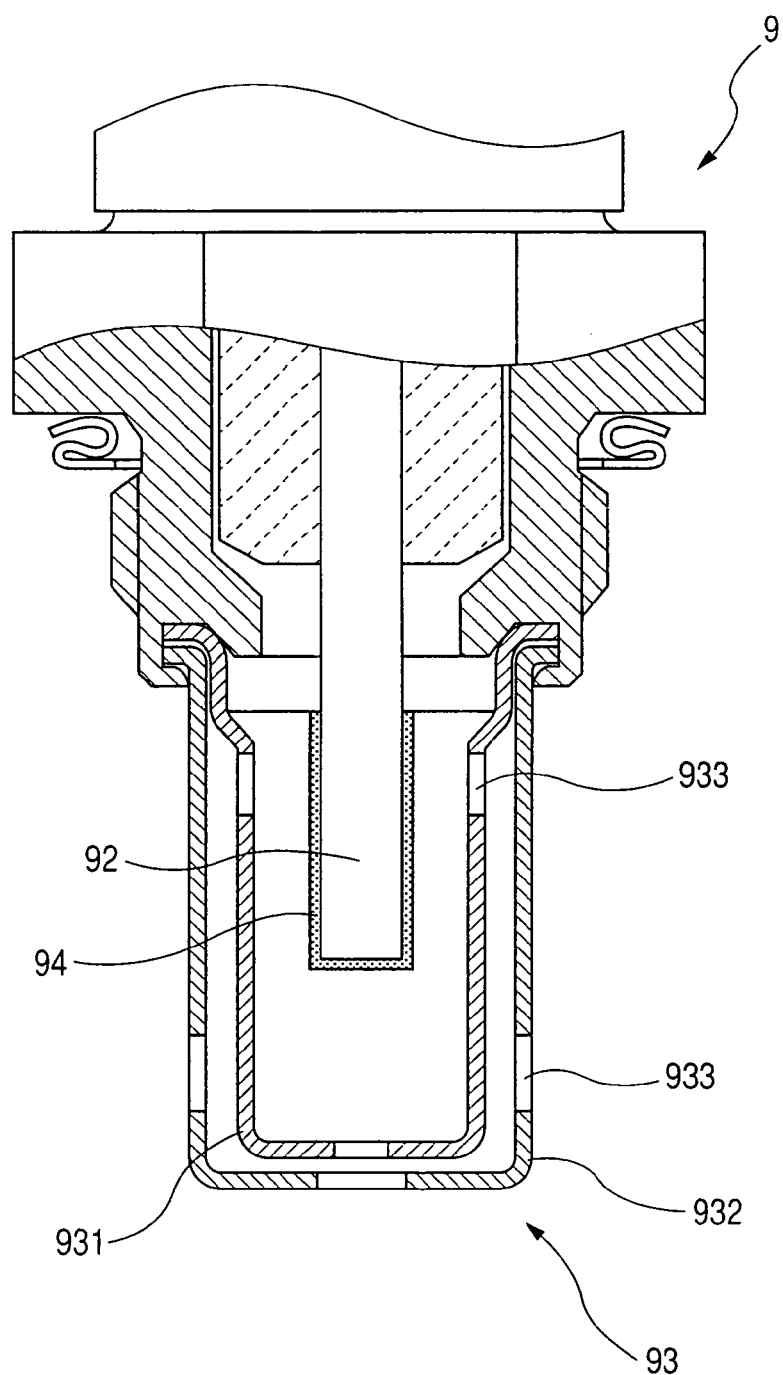
FIG. 20 is a longitudinal sectional view which shows another type of a conventional protective cover assembly of a gas sensor.
Figure 21:
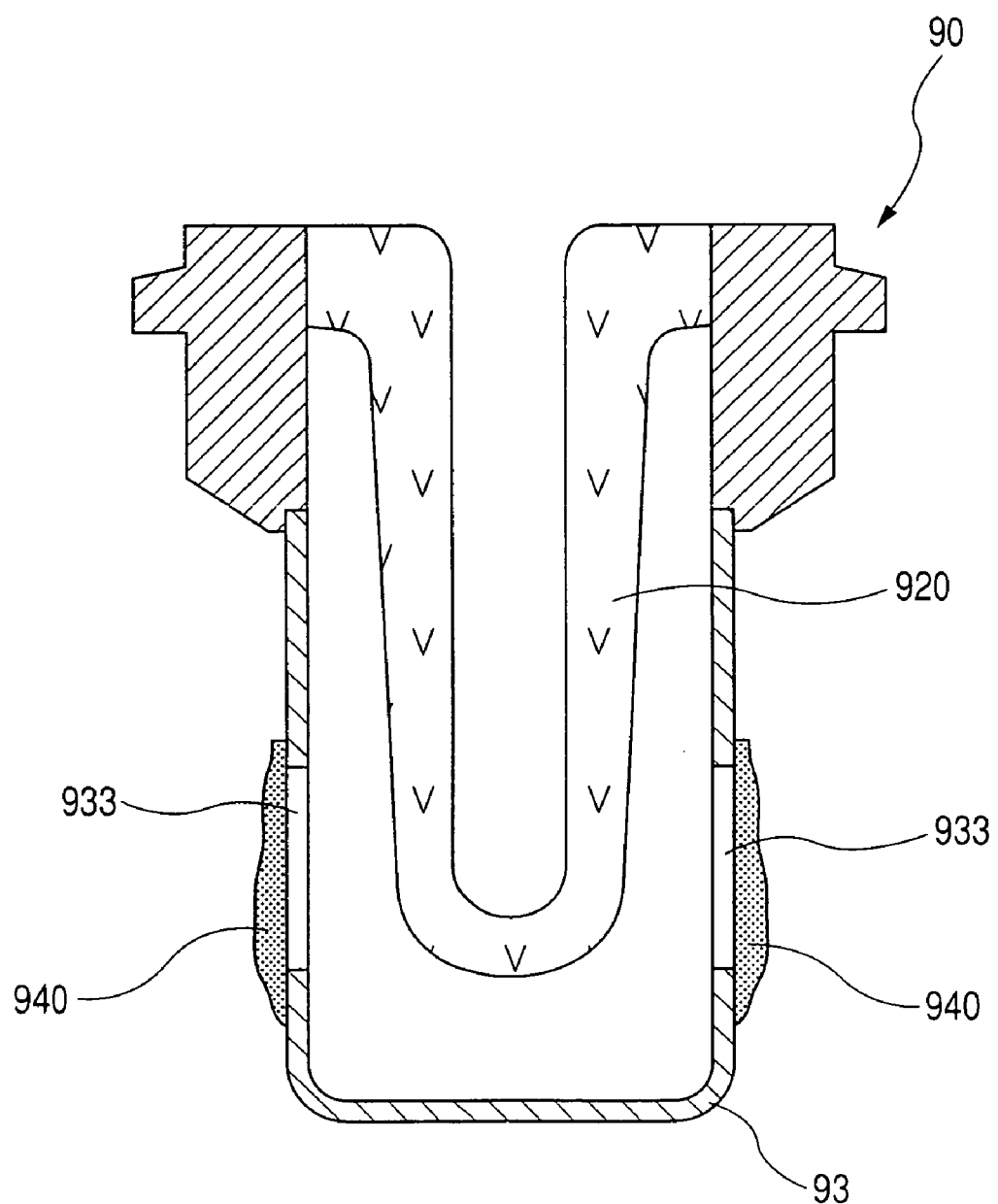
FIG. 21 is a longitudinal sectional view which shows another type of a conventional protective cover assembly of a gas sensor.

The structure of the protective cover assembly 4 of the gas sensor 1 of this embodiment eliminates the need for installation of the water-repellant protective film 94 on the gas sensor element 92, as illustrated in FIG. 20, and the protective layer 940 on the protective cover 93, as illustrated in FIG. 21, thus ensuring the responsiveness of the gas sensing element 2 without an increase in time required to activate the gas sensor element 2. The protective cover assembly 4 may, however, have any coating formed on the surface thereof for minimizing the entry of drops of water thereinto.

The gas outlet hole 422 is formed on the top end of the outer cover 42, thus avoiding the staying of water inside the outer cover 42, which ensures the durability of the protective cover assembly 4.

The gas outlet hole 412 of the inner cover 41, as can be seen from FIG. 3, works to draw the measurement gas G toward the top end of the protective cover assembly 4 as the gas stream G2 and discharge it therefrom. The flow of the measurement gas G passing outside and next to the gas outlet hole 412 produces the vacuum which promotes the entry of the measurement gas G having come inside the outer cover 42 into the inner cover 41 through the gas inlet holes 411 as the gas stream G2 with no drop of water. This prevents the gas sensor element 2 from being splashed with water.

The outer cover 42 has the frusto-conical wall 423, as can be seen from FIG. 3, serves to achieve smooth introduction of the gas stream G1 toward the gas outlet hole 422 between the outer and inner covers 42 and 41, thereby minimizing the intrusion of water into the inner cover 41.

The tapered shape of the wall 423 also serves to facilitate the ease of production of a smooth flow of the gas stream G1 and also of machining of the outer cover 42.

The inner cover 41 has, as described above, the frusto-conical walls 413 and 414 tapering to the top end thereof, thus facilitating the introduction of the gas stream G1 toward the gas outlet hole 422 between the outer and inner covers 42 and 41, which minimizes the intrusion of the water into the inner cover 41.

The tapered shape of the walls 413 and 414 also serves to facilitate the ease of production of the smooth flow of the gas stream G1 and also of machining of the inner cover 41.

The gas inlet holes 411 are formed in the frusto-conical wall 413, thus facilitating the orientation of the axial center line A with the vertical quadrature component Az extending toward the base end of the protective cover assembly 4 in the axial direction thereof.

The inner cover 41 has the upright wall 415 which extends in parallel to the lengthwise direction of the gas sensor 1 and faces the outer gas inlet holes 421, thereby facilitating the formation of the gas stream G1 directed in the lengthwise direction of the gas sensor 1 from the measurement gas G entering between the outer cover 42 and the inner cover 41 through one of the outer gas inlet holes 421, thereby promoting the formation of a smooth flow of drops of water which are higher in specific gravity than the measurement gas G in the lengthwise direction of the gas sensor 1 and discharging it from the gas outlet hole 422.

Figure 4:
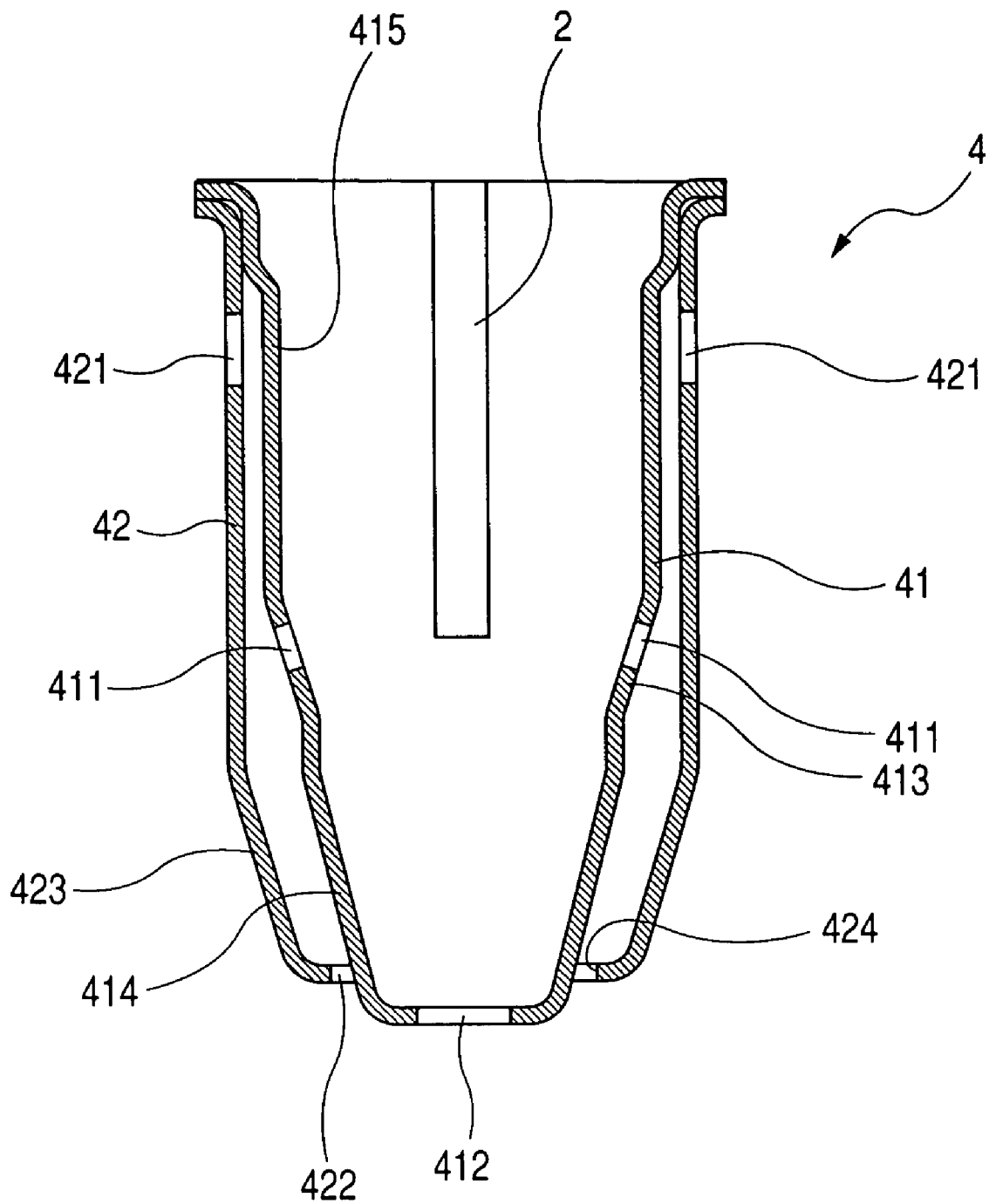
FIG. 4 is a longitudinal sectional view which shows a protective cover assembly according to the second embodiment of the invention.

FIG. 4 illustrates the protective cover assembly 4 according to the second embodiment of the invention.

The inner cover 41 has the tapered wall 413 located closer to the top end thereof than that in the first embodiment, as illustrated in FIG. 2. Specifically, the tapered wall 413 is located intermediate between the gas inlets 421 and the gas outlet hole 422 of the outer cover 42. The gas inlet holes 411 are formed in the tapered wall 413 and located at the middle between the gas inlets 421 and the gas outlet hole 422 of the outer cover 42.

The distance between each of the outer gas inlet holes 421 and one of the inner gas inlet holes 411 is greater than that in the first embodiment, thus enhancing the avoidance of entry of water into the inner cover 41 through the gas inlet holes 411 as compared with the structure of the first embodiment.

Other arrangements are identical with those in the first embodiment, and explanation thereof in detail will be omitted here.

Figure 5:
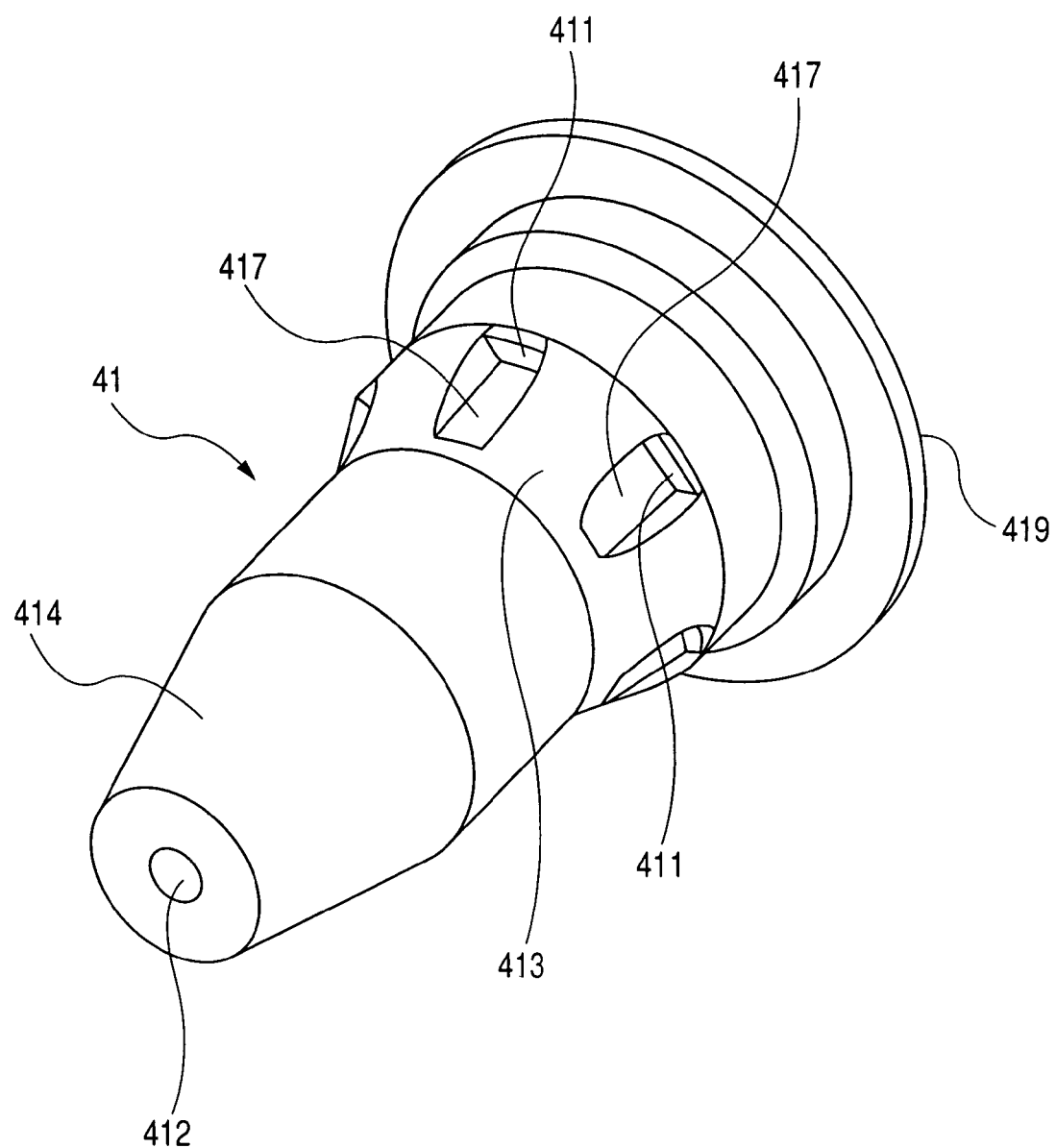
FIG. 5 is a perspective view which shows an inner cover of a protective cover assembly according to the third embodiment of the invention.
Figure 6:
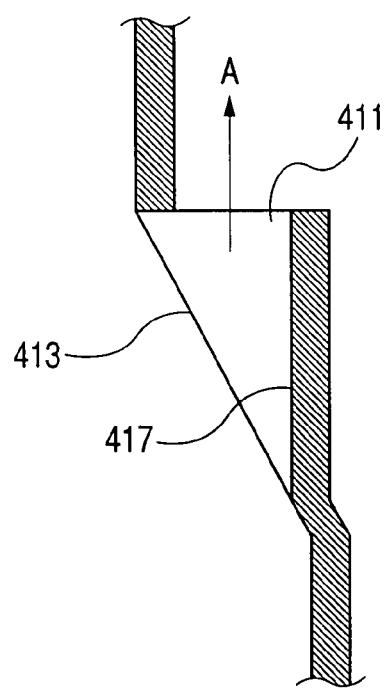
FIG. 6 is a partially sectional view which shows a gas inlet hole formed in the inner cover of FIG. 5.

FIGS. 5 and 6 illustrate the inner cover 41 of the protective cover assembly 4 according to the third embodiment of the invention.

The inner cover 41 has the same structure as the one in the first embodiment expect for the gas inlet holes 411.

Specifically, the inner cover 41 has dimples 417 formed in the tapered wall 413 at regular intervals in a circumferential direction thereof. Each of the gas inlet holes 411 are formed in the tapered wall 413 and opens toward the base end of the inner cover 41. Each of the dimples 417 leads to one of the gas inlet holes 411 and works as a louver.

Each of the gas inlet holes 411, as can be seen from FIG. 6, extends substantially perpendicular to the longitudinal center line of the inner cover 41. In other words, the axial center line A extends in parallel to the lengthwise direction of the protective cover assembly 4, thus decreasing the possibility of entry of water to the inner cover 41 through the gas inlet holes 411.

Other arrangements are identical with those in the first embodiment, and explanation thereof in detail will be omitted here.

Figure 7:
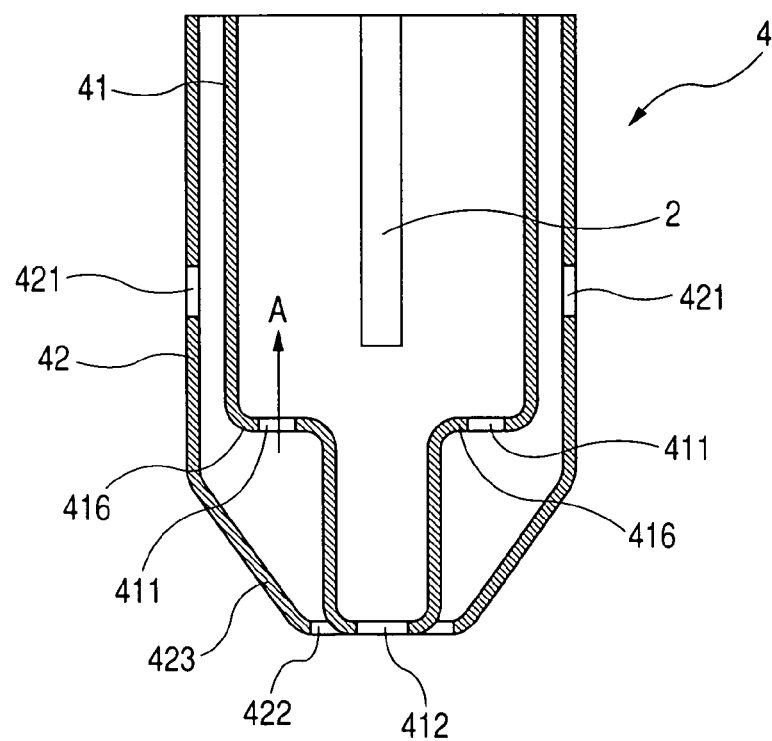
FIG. 7 is a longitudinal sectional view which shows a protective cover assembly according to the fourth embodiment of the invention.

FIG. 7 illustrates the protective cover assembly 4 according to the fourth embodiment of the invention.

The inner cover 41 has an annular shoulder 416 extending substantially perpendicular to the length of the gas sensor 1 (i.e., the longitudinal center line of the protective cover assembly 4) and the gas inlet holes 411 formed in the shoulder 416. The axial center line A of each of the gas inlet holes 411, like the third embodiment, is oriented in parallel to the lengthwise direction of the protective cover assembly 4.

The inner cover 41 has the end face which lies in flush with the end face of the outer cover 42.

The geometry of the inner cover 41 serves to create a stream of the measurement gas which is introduced between the outer cover 42 and the inner cover 41 and enters inside the inner cover 41 through the gas inlet holes 411 (i.e., the gas stream G2 in FIG. 3) and which is more complex than that in the first embodiment, thus decreasing the possibility of entry of water to the inner cover 41 through the gas inlet holes 411 greatly.

Other arrangements are identical with those in the first embodiment, and explanation thereof in detail will be omitted here.

The annular shoulder 416 may alternatively be designed to extend close to the base end (i.e., an upper end, as viewed in the drawing) of the protective cover assembly 4 as approaching inwardly in a radius direction of the inner cover 41.

Figure 8:
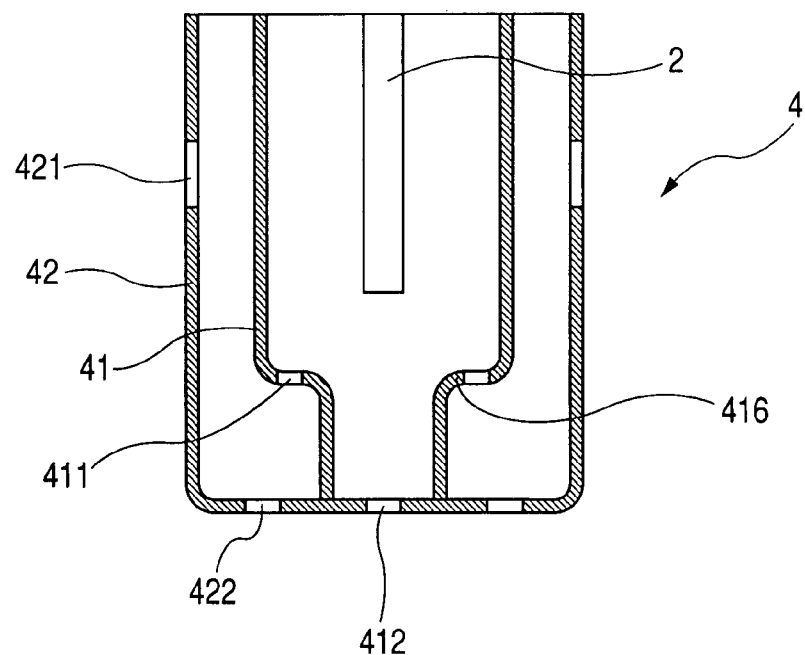
FIG. 8 is a longitudinal sectional view which shows a protective cover assembly according to the fifth embodiment of the invention.

FIG. 8 illustrates the protective cover assembly 4 according to the fifth embodiment of the invention.

The outer cover 42 is of a cylindrical cup-shape with a side wall extending straight. The inner cover 41 has, like the fourth embodiment in FIG. 7, the annular shoulder 416 and a top edge placed in abutment with an inner wall of the top end of the outer cover 42. Other arrangements are identical with those in the first embodiment, and explanation thereof in detail will be omitted here.

Figure 9:
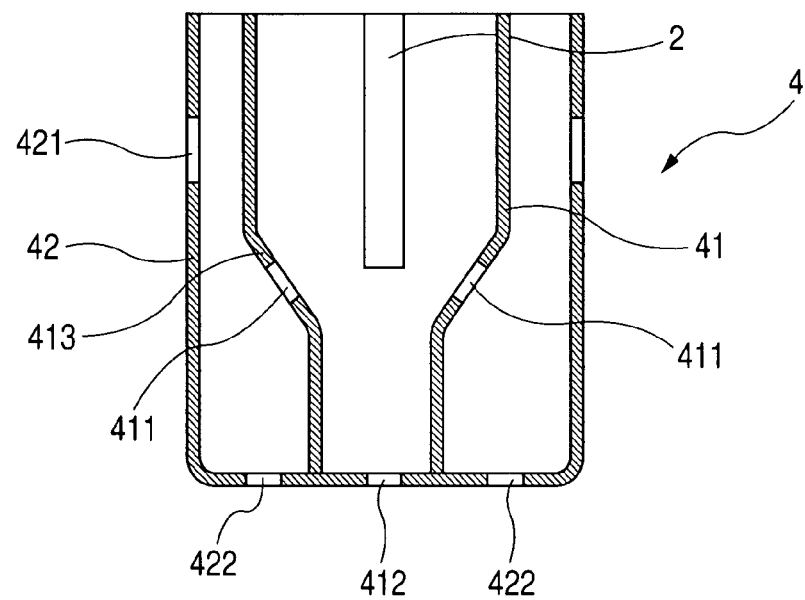
FIG. 9 is a longitudinal sectional view which shows a modification of the protective cover assembly of FIG. 8.

FIG. 9 illustrates a modification of the structure in FIG. 8. The inner cover 41 has the tapered wall 413 in which the gas inlet holes 411 are formed instead of the shoulder 416 in FIG. 8.

The inventor of this application performed tests to evaluate the effect of keeping the gas sensor element 2 free from the adhesion of drops of water.

Figure 19:
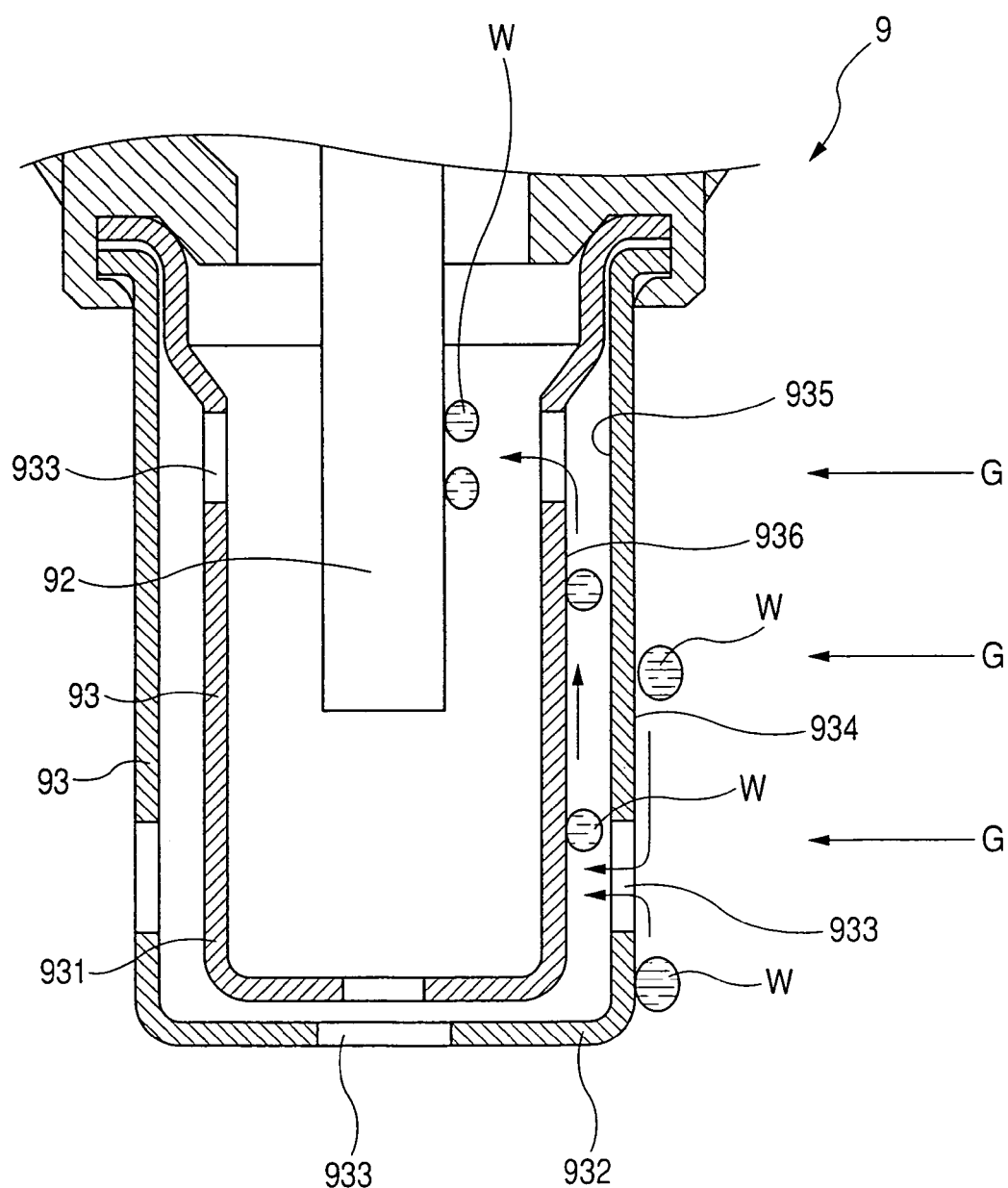
FIG. 19 is a longitudinal sectional view which shows a conventional protective cover assembly of a gas sensor.

The inventor prepared as test samples the gas sensor 1 having the structure, as illustrated in FIGS. 1 to 3, and the gas sensor 9, as illustrated in FIG. 19.

Figure 10:
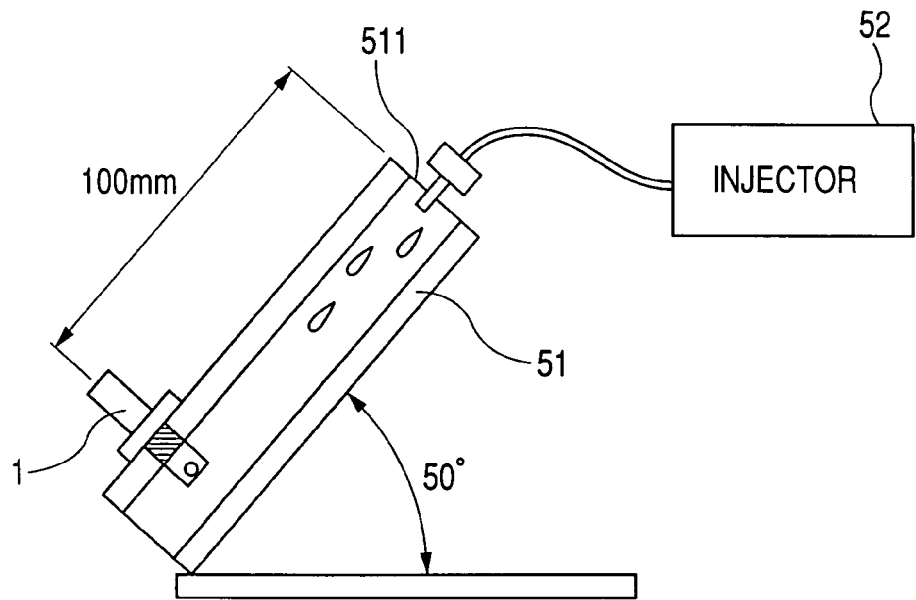
FIG. 10 is a side view which shows a test machine used to evaluate the effect of keeping the gas sensor element of FIG. 1 free from the adhesion of drops of water.

Next, the inventor installed the gas sensor 1 in a pipe 51, as illustrated in FIG. 10, which had an inner diameter of 35 mm and was inclined at 50° to the horizontal plane. The distance between the gas sensor 1 and an upper open end 511 of the pipe 51 was 100 mm. Air containing drops of water was injected from the upper open end 511 using an injector 52 five times. The content of water in each jet of the air was 0.2 ml. The pressure of the jet of air was 0.15 kg/cm$^2$.

Figure 11:
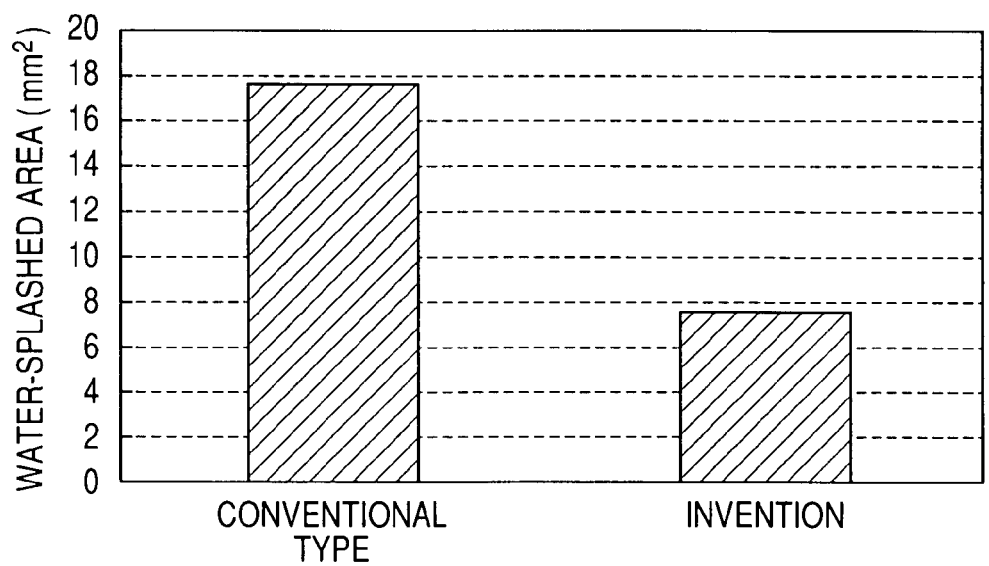
FIG. 11 is a graph which shows results of tests as performed using the test machine of FIG. 10.

The inventor measured a total area of the gas sensor element 2 built in the gas sensor 1 which was splashed with water. The same test was performed on the gas sensor 9. Results of the tests are shown in a graph of FIG. 11. The graph shows that the water-splashed area of the gas sensor 1 is less than half that of the gas sensor 9.

The inventor also performed tests to evaluate the responsiveness of the gas sensor 1.

Figure 12A:
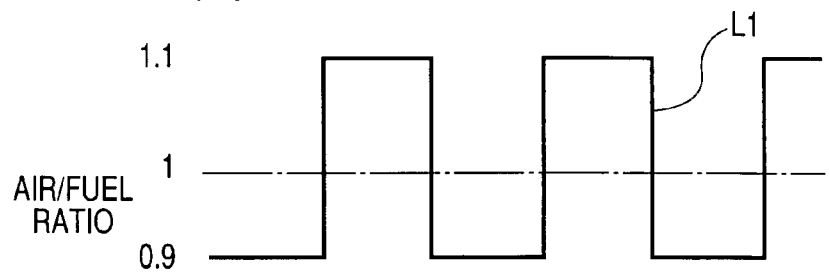
FIGS. 12(a) and 12(b) are views which show a relation between a change in air-fuel ratio and an output of a gas sensor in tests performed to evaluate the responsiveness of the gas sensor of FIG. 1.
Figure 12B:
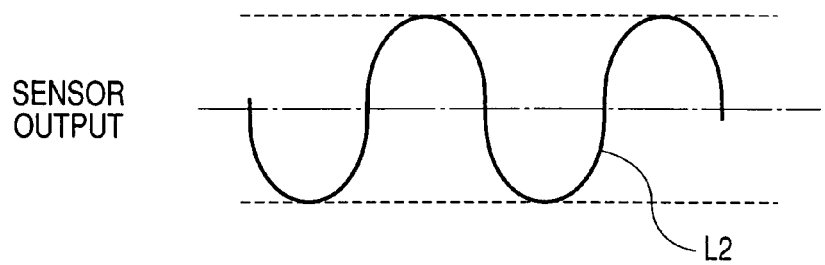
Figure 13:
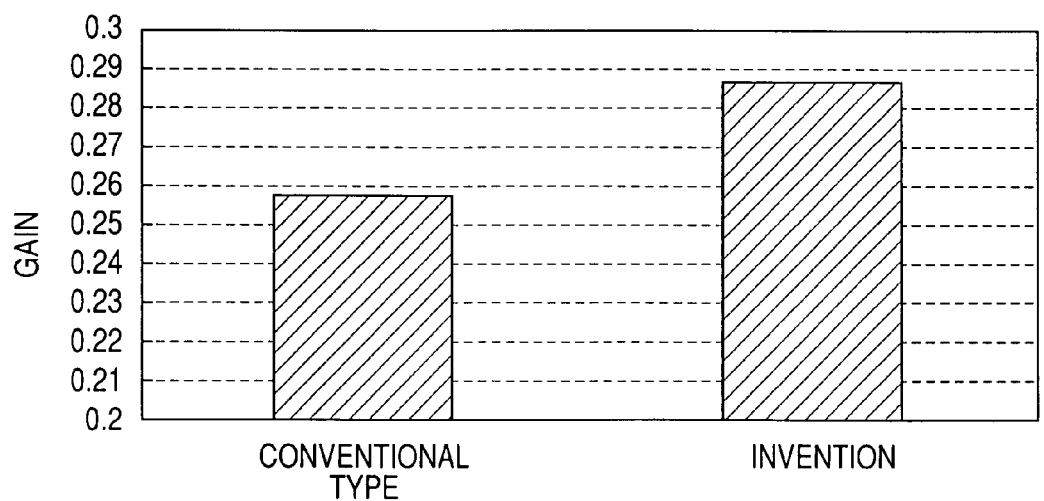
FIG. 13 is a graph which shows gains of outputs of the gas sensor, as used in the tests in FIGS. 12(a) and 12(b), and a conventional gas sensor.

First, the inventor installed the gas sensor 1 in an exhaust pipe of an inline six-cylinder direct-injection engine and run the engine at 2000 rpm. The inventor controlled, as represented by a line L1 in FIG. 12(a), the air-fuel ratio to change in the excess air ratio between 0.9 and 1.1 at a cycle of 4.16 Hz. The temperature of the gas sensor element 2 was 750° C. A change in output of the gas sensor 1 during the test is represented by a line L2 in FIG. 12(b). The inventor analyzed the change in output of the gas sensor 1 (L2) arising from the change in air-fuel ratio (L1) and evaluate the gain thereof. The same test was performed on the gas sensor 9, as illustrated in FIG. 19. Results of tests are shown in a graph of FIG. 13.

The graph shows that the gas sensor 1 is higher in gain than the gas sensor 9 and excellent in the responsiveness.

Figure 14:
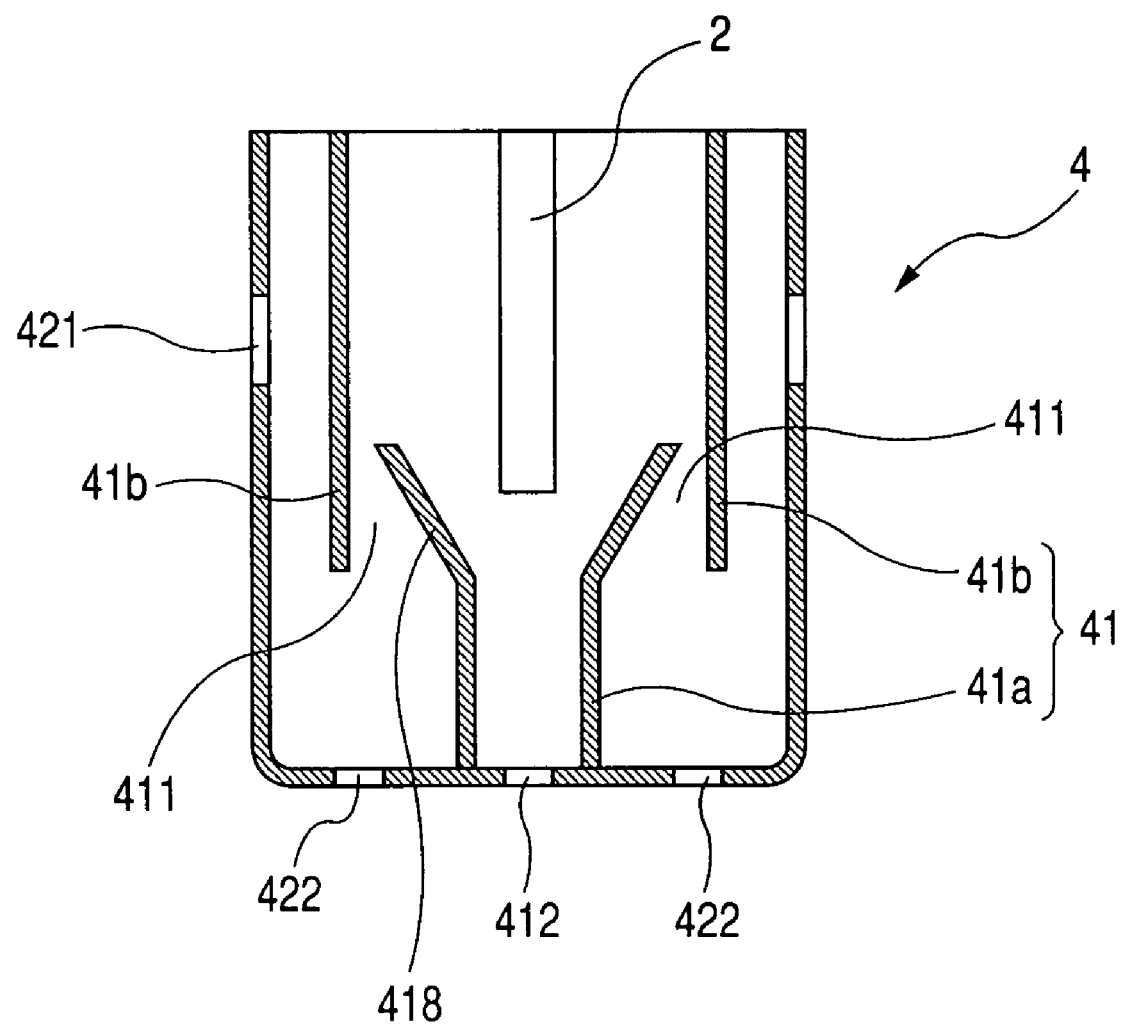
FIG. 14 is a longitudinal sectional view which shows a protective cover assembly according to the sixth embodiment of the invention.

FIG. 14 shows the protective cover assembly 4 according to the sixth embodiment of the invention.

The inner cover 41 is made up of two parts: a funnel-shaped cylinder 41a and a hollow straight cylinder 41b. The funnel-shaped cylinder 41a has the gas outlet hole 412 formed on the top end thereof and a horn aperture 418 expanding toward the gas sensor element 2.

The straight cylinder 41b extends from the base end of the protective cover assembly 4 to surround the inner cover 41 partially. The top end of the straight cylinder 41b is located closer to the top end of the protective cover assembly 4 than the base end of the funnel-shaped cylinder 41a. In other words, a top end portion of the straight cylinder 41b overlap a base end portion of the funnel-shaped cylinder 41a in a radius direction of the protective cover assembly 4 to define an annular gas inlet 411.

Other arrangements are identical with those in the fifth embodiment of FIG. 9.

Figure 15A:
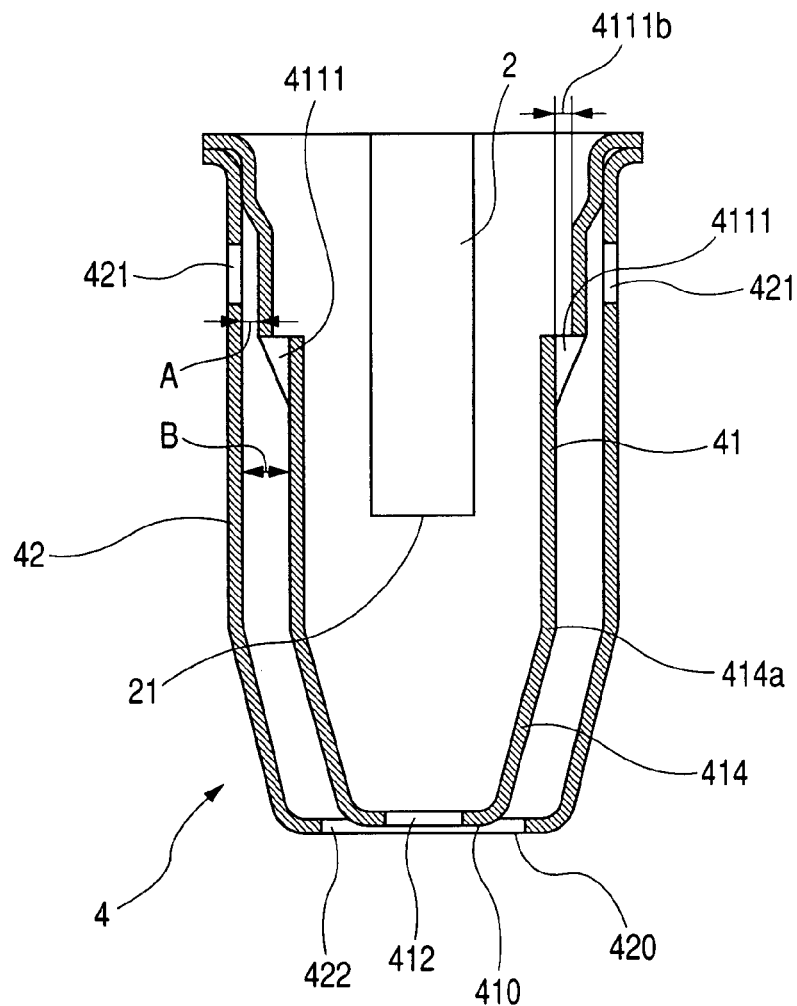
FIG. 15(a) is a longitudinal sectional view which shows a protective cover assembly according to the seventh embodiment of the invention.
Figure 16:
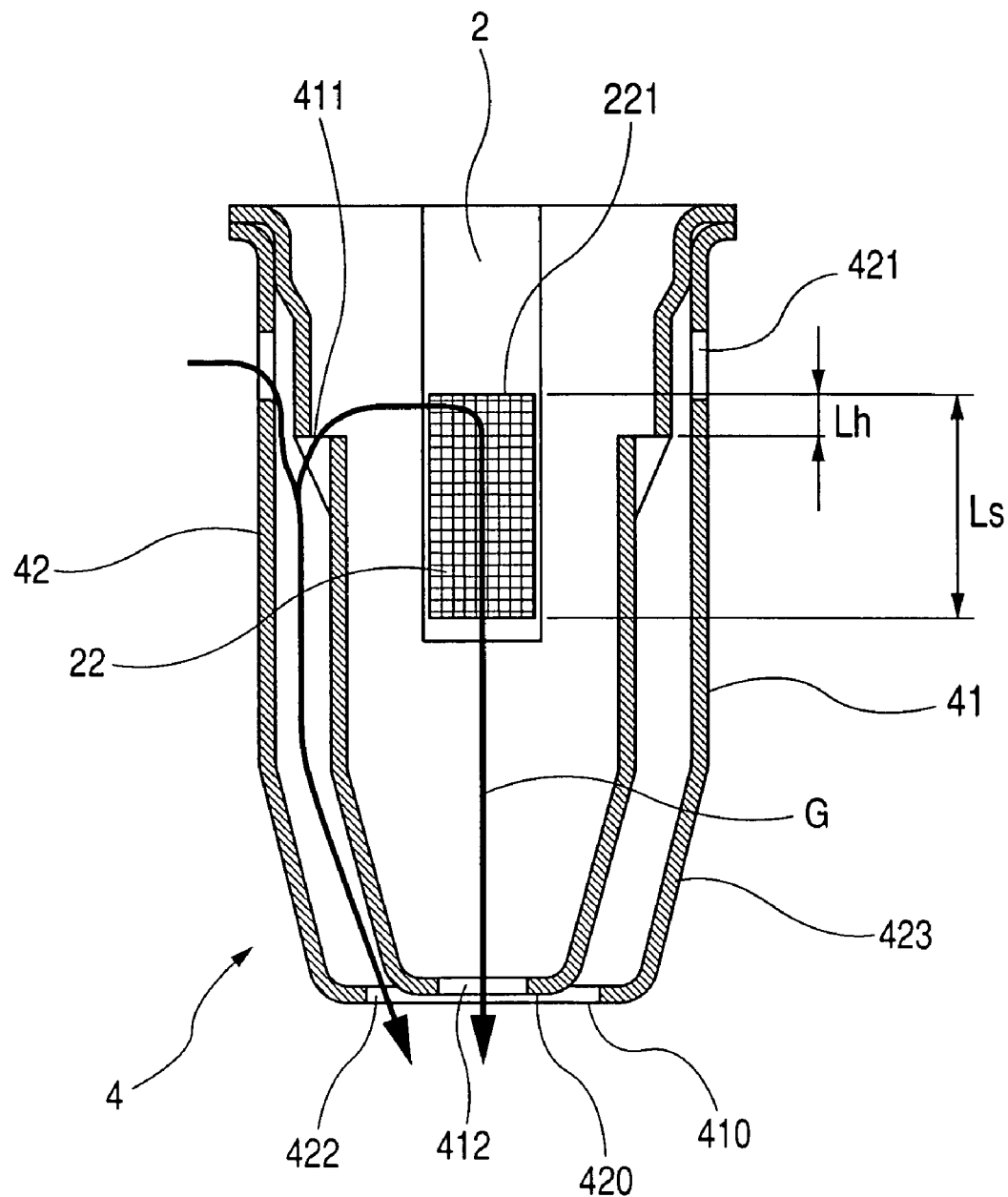
FIG. 16 is a longitudinal sectional view which shows flows of streams of gas within the protective cover assembly of FIG. 15.

FIGS. 15(a) and 16 show the protective cover assembly 4 according to the seventh embodiment of the invention which is a modification of the first and third embodiments. The inner cover 41 has the top face 410 lying in flush with the top face 420 of the outer cover 42.

In FIGS. 15(a) and 16, the top face 410 of the inner cover 41 is illustrated as being shifted slightly toward the base end of the protective cover assembly 4 from the top face 420 of the outer cover 42. Such a misalignment is within a tolerance. The tolerance is, however, determined only to permit the top face 410 to be located inside the top face 420.

The tapered wall 414 of the inner cover 41 including a portion of the inner cover 41 having a minimum diameter is located closer to the top end of the protective cover assembly 4 than the top end of the gas sensor element 2.

The outer cover 42 has six outer gas inlet holes 421 formed at a regular interval over the whole of circumference thereof. Each of the outer gas inlets 421 has a diameter of 2 mm. The outer cover 42 has also formed in the bottom thereof a circular hole which defines an annular or doughnut-shaped gas outlet hole 422 around the outer edge of the top face 410 of the inner cover 41. The clearance between the inner edge of the top face 420 of the outer cover 42 and the outer edge of the top face 410 of the inner cover 41, that is, the width of the gas outlet hole 422 is 0.5 mm.

The clearance A between the inner wall of the outer cover 42 at the outer gas inlet holes 421 and the outer wall of the inner cover 41 facing the outer gas inlet holes 421 is 0.5 mm. The clearance B between the inner wall of the outer cover 42 and the outer wall of the inner cover 41 beneath the inner gas inlets 4111 formed in the inner cover 41 is 1.5 mm.

Figure 15B:
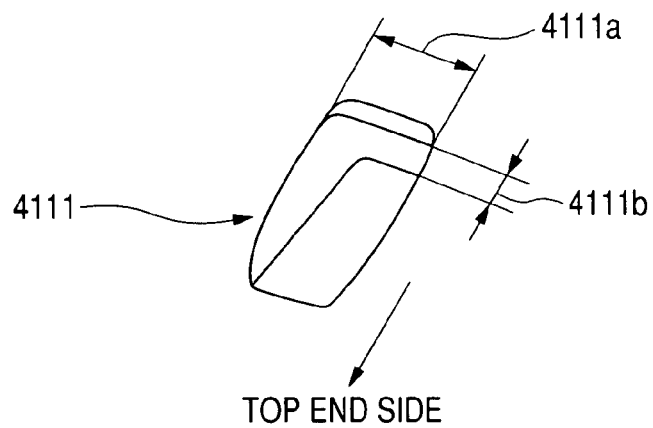
FIG. 15(b) is a perspective view which shows an inner gas inlet hole formed in an inner cover of the protective cover assembly of FIG. 15(a)

The gas outlet hole 412 of the inner cover 41 has a diameter of 1.5 mm. Each of the inner gas inlet holes 4111 has a configuration, as illustrated in FIG. 15(b).

The six inner gas inlet holes 4111 are arrayed at an regular interval around the whole of circumference of the inner cover 41. Each of the inner gas inlet holes 4111 is, as clearly illustrated in FIG. 15(b), formed by cutting the side surface of the inner cover 41 and pressing it inwardly. The width 4111a of the inner gas inlet holes 4111 is 2 mm. The depth 4111b of the inner gas inlet holes 4111, as can be seen from FIGS. 15(a) and 15(b), that is the size thereof in a direction perpendicular to the longitudinal center lien of the protective cover assembly 4 is 0.5 mm.

Each of the inner gas inlet holes 4111 may be designed to have the angle θ, as defined in FIG. 2, which is 90° to further increase a difficulty for drops of water contained in the measurement gas G to enter the inner cover 41, thereby minimizing the splashing of the gas sensor element 2 with water.

The gas sensor element 2, as clearly illustrated in FIG. 16, has affixed to the surface thereof a measurement gas electrode 22 to be exposed to the measurement gas. The inner gas inlet holes 411 are, as clearly illustrated in FIG. 16, located within a distance between the base end 221 of the measurement gas electrode 22 and the center of the measurement gas electrode 22 in the lengthwise direction thereof. More preferably, the inner gas inlet holes 411 are located within one third of the length of the measurement gas electrode 22 in the lengthwise direction of the gas sensor element 2 from the base end 221. Other arrangements are identical with those in the first and third embodiment.

The structure of this embodiment offers the following advantages.

If the top face 410 of the inner cover 41 is located outside the top face 420 of the outer cover 42, it may cause drops of water flowing from the lateral direction of the gas sensor 1 together with the measurement gas to hit the side of the inner cover 41 and then enter at the gas outlet hole 422 into the clearance between the inner cover 41 and the outer cover 42. In order to alleviate this problem, the top face 410 is placed flush with or slightly inside the top face 420, thereby minimizing the splashing of the gas sensor element 2 with water.

If the top face 410 of the inner cover 41 is located inside the top face 420 of the outer cover 42, it results in an increased difficulty in creating a stream of the measurement gas flowing out of the gas outlet hole 412 formed in the top face 410 of the inner cover 41. It is, thus, advisable that the top face 410 of the inner cover 41 be located flush with or slightly inside the top face 420 of the outer cover 42 within the tolerance of the gas sensor 1.

Figure 17:
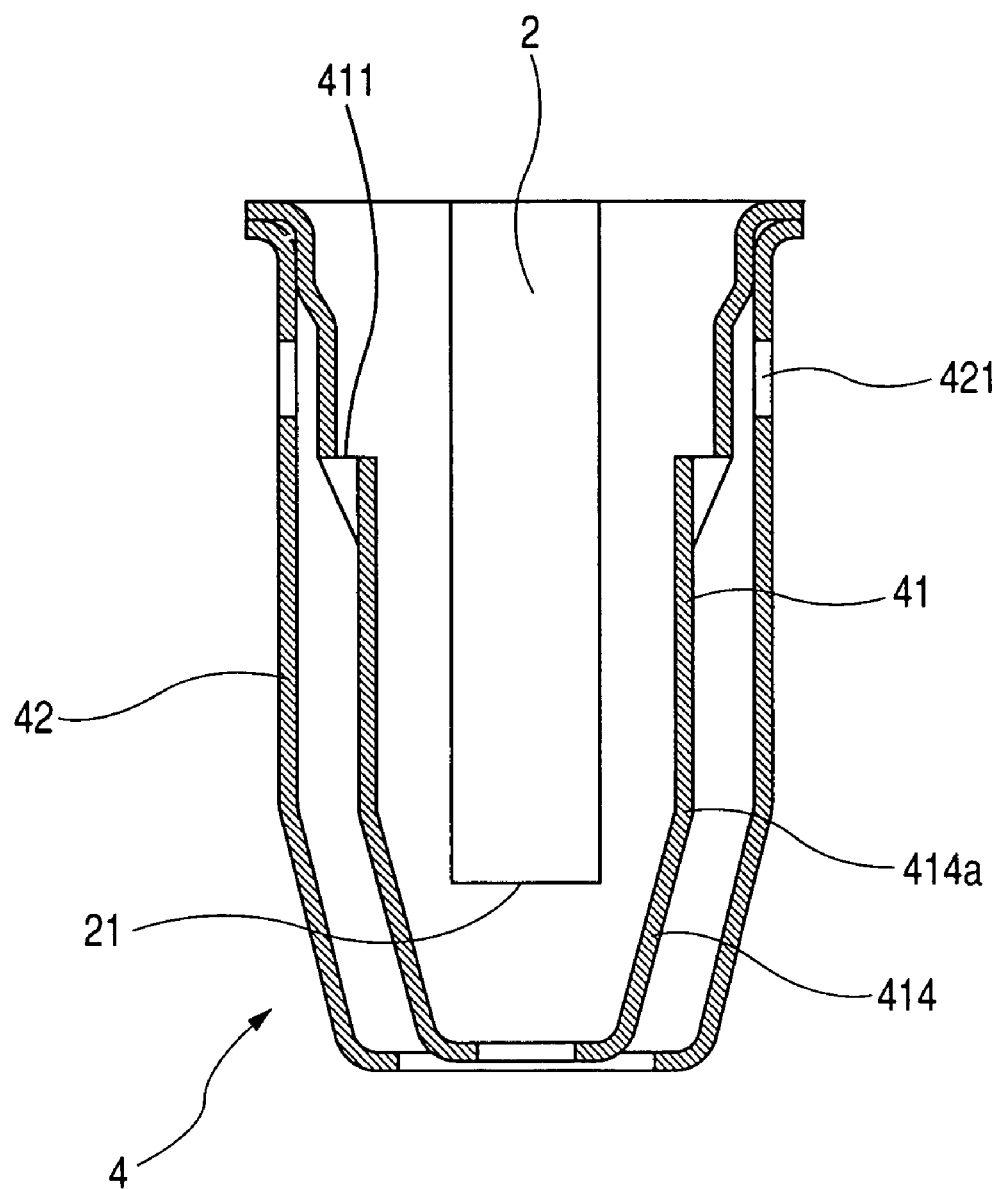
FIG. 17 is a longitudinal sectional view which shows a comparative example of a protective cover assembly for explaining the advantage of the structure of FIG. 16.

The tapered wall 414 of the inner cover 41 is located at a base end 414a thereof closer to the top end of the gas sensor 1 than the top end 21 of the gas sensor element 2, thereby minimizing the physical interference of the gas sensor element 2 with the inner wall of the inner cover 41. Specifically, if the base end 414a of the tapered wall 414 of the inner cover 41 is, as demonstrated in FIG. 17, located closer to the base end of the gas sensor 1 than the top end 21 of the gas sensor element 2, the top end 21 will lie inside the wall 414 tapering toward the top end of the protective cover assembly 4, so that the interval between the top end 21 of the gas sensor element 2 and the inner wall of the inner cover 41 will be smaller than that in FIG. 15, thus resulting in an increased possibility of the interference of the gas sensor element 2 with the inner cover 41, for example, when the gas sensor element 2 is subjected to mechanical vibrations. In order to alleviate this problem, the inner cover 41 is designed to have the base end 414a of the tapered wall 414 located closer to the base end of the gas sensor 1 (i.e., the protective cover assembly 4) than the top end 21 of the gas sensor element 2.

The inner gas inlet holes 411 are, as described above, located within half the length of the measurement gas electrode 22 from the base end 221, thereby ensuring, as illustrated in FIG. 16, quick reach of the measurement gas G having entered at the gas inlet holes 411 to the measurement gas electrode 22 and the exposure of the whole of the measurement gas electrode 22 to the measurement gas G. This enhances the responsiveness of the gas sensor 1.

If the inner gas inlet holes 411 are located within a half of the length of the measurement gas electrode 22 leading to the top end thereof, it result in an increased difficulty in exposure of the whole of the measurement gas electrode 2 to the measurement gas G having entered at the inner gas inlet holes 411, which may compromise the responsiveness of the gas sensor 1. Alternatively, if the inner gas inlet holes 411 are located closer to the base end of the protective cover assembly 4 than the base end 221 of the measurement gas electrode 22, it will result in an increased time required for the measurement gas G having entered at the inner gas inlet holes 41 1 to reach the measurement gas electrode 22, which also compromise the responsiveness of the gas sensor 1.

The inventor of this application performed tests to evaluate the responsiveness of the gas sensor 1 in terms of a locational relationship between the gas inlet holes 411 of the inner cover 41 and the measurement gas electrode 22 of the gas sensor element 2.

First, the inventor prepared test samples of the gas sensor 1 in which Lh/Ls is 1/3, 1/2, 2/3, and 4/5 where Ls is, as illustrated in FIG. 16, the length of the measurement gas electrode 22 in the axial direction of the gas sensor element 2, and Lh is the distance between the base end 221 of the measurement gas electrode 22 and the gas inlet holes 411. Next, the inventor performed the tests in the same manner as described with reference to FIGS. 12(a) to 13.

Figure 18:
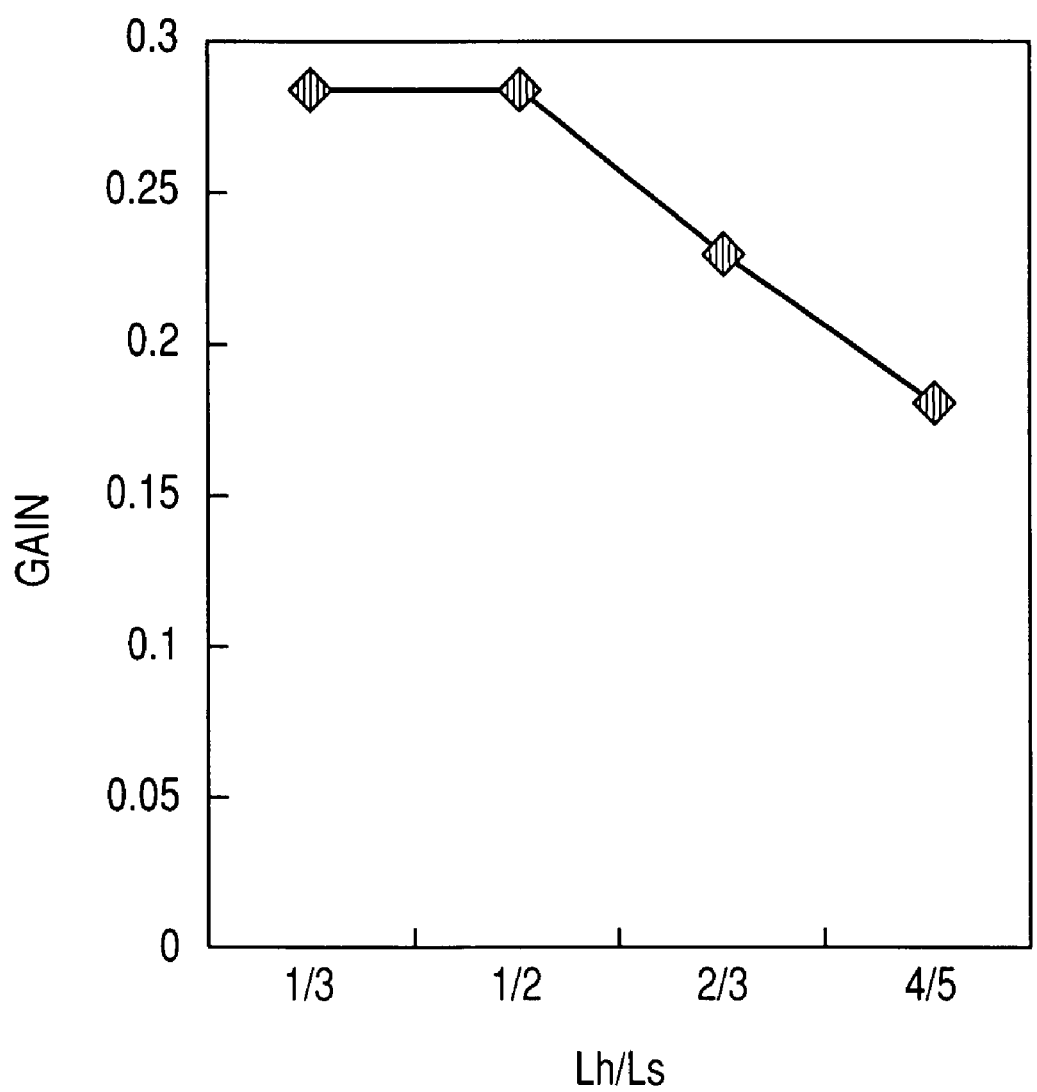
FIG. 18 is a graph which shows results of tests performed to evaluate the responsiveness of a gas sensor in terms of a locational relationship between gas inlet holes of an inner cover and a measurement gas electrode of a gas sensor element of the invention.

Results of the tests are illustrated in FIG. 18. The graph shows that the test samples where Lh/Ls is 1/3 and 1/2, meaning that the inner gas inlet holes 411 are located within half the length of the measurement gas electrode 22 from the base end 221 have a gain of 0.285 which is great enough to ensure the responsiveness of the gas sensor 1 and that it is advisable that Lh/Ls be less than or equal to 1/3 in light of the production tolerance of the gas sensor 1.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor having a length with a base end and a top end opposite the base end comprising:
    a gas sensor element having a sensing portion sensitive to a concentration of a gas to be measured to provide a signal indicative thereof;
    a housing having a base end and a top end opposite the base end, said housing having said gas sensor element retained therein;
    a cover assembly having a base end and a top end which is opposite the base end and close to the top end of the gas sensor, said cover assembly including an outer cover and an inner cover disposed inside the outer cover, said cover assembly being joined at the base end thereof to the top end of said housing to place the sensing portion of said gas sensor element within the inner cover;
    an outer gas inlet formed in a peripheral wall of the outer cover of said cover assembly;
    an outer gas outlet formed in a portion of the outer cover of said cover assembly which is located closer to the top end of said cover assembly than said outer gas inlet; and
    an inner gas inlet formed in a portion of the inner cover of said cover assembly which is located closer to the top end of said cover assembly than said outer gas inlet, said inner gas inlet being formed by an opening which is so shaped as to have an axial center line that is oriented from outside to inside the inner cover and defined to have a vertical quadrature component oriented in a rectangular coordinate system toward the base end of the gas sensor in an axial direction of the gas sensor,
    wherein the axial center line of the opening is defined to have said vertical quadrature component and a transverse quadrature component which is oriented toward and perpendicular to a longitudinal axis of the gas sensor that extends in the axial direction of the gas sensor, the transverse quadrature component being perpendicular to the vertical quadrature component, and wherein an angle which the axial center line of the inner gas inlet opening makes with the transverse quadrature component is 30° or more, wherein said gas sensor element has affixed to a surface thereof a measurement gas electrode which is to be exposed to the gas to be measured, the measurement gas electrode having a length with a base end and a top end which is opposite the base end thereof and faces the top end of said cover assembly, and wherein the inner gas inlet is located within half the length of the measurement gas electrode from the base end of the measurement gas electrode.

2. A gas sensor as set forth in claim 1, wherein said outer gas outlet is formed in a top end of the outer cover.

3. A gas sensor as set forth in claim 2, wherein the inner cover and the outer cover both have top ends which lie flush with each other to define the top end of said cover assembly.

4. A gas sensor as set forth in claim 1, wherein the inner cover has a top end located far away from the base end of said cover assembly, and further comprising an inner gas outlet formed in the top end of the inner cover.

5. A gas sensor as set forth in claim 1, wherein the outer cover of said cover assembly has at least one wall having a diameter which decreases as approaching the top end of said cover assembly.

6. A gas sensor as set forth in claim 5, wherein the at least one wall tapers toward the top end of said cover assembly.

7. A gas sensor as set forth in claim 1, wherein the inner cover of said cover assembly has at least one wall having a diameter which decreases as approaching the top end of said cover assembly.

8. A gas sensor as set forth in claim 7, wherein the at least one wall tapers toward the top end of said cover assembly.

9. A gas sensor as set forth in claim 7, wherein the at least one wall of the inner cover includes a portion of the inner cover which is the smallest in diameter and is located closer to the top end of the gas sensor than a top end of said gas sensor element facing the top end of the gas sensor.

10. A gas sensor as set forth in claim 1, wherein the axial center line includes the vertical quadrature component and a transverse quadrature component which is oriented perpendicular to the axial direction of the gas sensor.

11. A gas sensor as set forth in claim 1, wherein the inner cover has formed in a peripheral wall thereof a recess having a base end oriented toward the base end of said cover assembly, and wherein the inner gas inlet is formed in the base end of the recess.

12. A gas sensor as set forth in claim 1, wherein the inner cover has a side surface which faces the outer gas inlet formed in the cover and extends in parallel to the axial direction of the gas sensor.

* * * * *